US012697097B2

(12) United States Patent
Evertsson et al.

(10) Patent No.: US 12,697,097 B2
(45) Date of Patent: Aug. 4, 2026

(54) MAGNETOMOTIVE PROBE AND METHOD OF USE THEREOF

(71) Applicant: NanoEcho AB, Lund (SE)

(72) Inventors: Maria Evertsson, Lund (SE); Tomas Jansson, Lund (SE)

(73) Assignee: NanoEcho AB, Lund (SE)

( * ) Notice: Subject to any disclaimer, the term of this patent is extended or adjusted under 35 U.S.C. 154(b) by 376 days.

(21) Appl. No.: 18/024,226

(22) PCT Filed: Sep. 6, 2021

(86) PCT No.: PCT/EP2021/074526
§ 371 (c)(1),
(2) Date: Mar. 1, 2023

(87) PCT Pub. No.: WO2022/049297
PCT Pub. Date: Mar. 10, 2022

(65) Prior Publication Data
US 2023/0293152 A1     Sep. 21, 2023

(30) Foreign Application Priority Data

Sep. 4, 2020    (EP) .................................... 20194483

(51) Int. Cl.
*A61B 8/00*          (2006.01)
*A61B 8/08*          (2006.01)
(Continued)

(52) U.S. Cl.
CPC .............. *A61B 8/481* (2013.01); *A61B 8/085* (2013.01); *A61B 8/12* (2013.01); *A61K 49/1818* (2013.01)

(58) Field of Classification Search
CPC ..................................................... A61B 8/481
See application file for complete search history.

(56) References Cited

U.S. PATENT DOCUMENTS 11,850,097 B2 * 12/2023 Cinthio ................... A61B 8/54
2009/0043198 A1     2/2009 Milner et al.
(Continued)

FOREIGN PATENT DOCUMENTS

EP           2801323 A1 * 11/2014  ............. A61B 8/481
JP      2008220530 A     9/2008
(Continued)

OTHER PUBLICATIONS

Japanese Office Action, Notice of Reasons for Rejection mailed Jun. 3, 2025 for JP2023-515250.
(Continued)

*Primary Examiner* — Joseph M Santos Rodriguez
(74) *Attorney, Agent, or Firm* — Veros Legal Solutions, LLP

(57)          ABSTRACT
A magnetomotive imaging probe device and method is described. The probe device includes a housing having an outer surface and an inner cavity; a magnet; a sensing device configured to detect distance, movement, or magnetic material. The magnet is arranged in the inner cavity of the housing and the sensing device on the outer surface of the housing, and the magnet is arranged to generate a time-varying magnetic field at an imaging plane of the sensing device. The magnet is intended to move magnetic nanoparticles in tissue such that a movement can be detected with the sensing device (ultrasound, optical or other). The detected motion infers the presence of magnetic material (nanoparticles).

20 Claims, 6 Drawing Sheets

(51) Int. Cl.
    *A61B 8/12*         (2006.01)
    *A61K 49/18*     (2006.01)

(56)            References Cited

U.S. PATENT DOCUMENTS

| | | | | |
|---|---|---|---|---|
| 2012/0118052 A1* | 5/2012 | O'Donnell | ......... | G01N 29/2418 |
| | | | | 73/64.53 |
| 2012/0226093 A1* | 9/2012 | Creighton | ........ | A61B 17/22012 |
| | | | | 977/773 |
| 2019/0209135 A1* | 7/2019 | Cinthio | ................ | A61B 8/4209 |
| 2023/0293152 A1* | 9/2023 | Evertsson | ................ | A61B 8/12 |
| | | | | 600/458 |

FOREIGN PATENT DOCUMENTS

| | | | |
|---|---|---|---|
| JP | 2011507561 A | 3/2011 |
| JP | 2016516559 A | 6/2016 |
| WO | 2009073748 A1 | 6/2009 |
| WO | 2014180854 A1 | 11/2014 |

OTHER PUBLICATIONS

International Search Report from PCT/EP2021/074526 filed Sep. 6, 2021 (Sep. 6, 2021) dated Nov. 28, 2021.
Mariappan Leo et al: Magneto acoustic tomography with short pulsed magnetic field for in-vivo imaging of magnetic iron oxide nanoparticles11 , Nanomedicine , Nanotechnology , Biology and Medicine, Elsevier, NL, vol. 12, No. 3, Dec. 2, 2015 (Dec. 2, 2015), pp. 689-699, XP029474149, ISSN: 1549-9634, DOI:10.1016/J. NANO.2015.10.014 abstract figures 1-7, p. 689-p. 697.
Written Opinion from PCT/EP2021/074526 filed Sep. 6, 2021 (Sep. 6, 2021).
Xu Liufang; Second Examination Opinion Notice; Oct. 30, 2025; pp. 1-12.

* cited by examiner

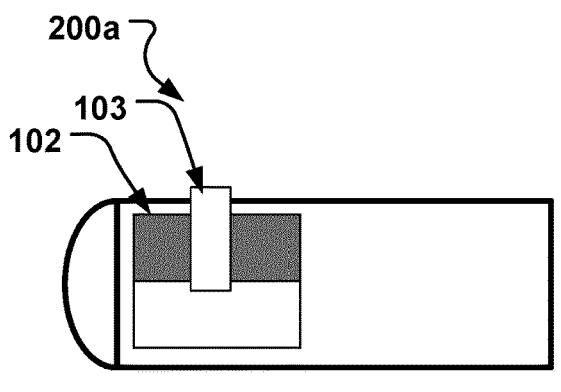
Fig. 2A
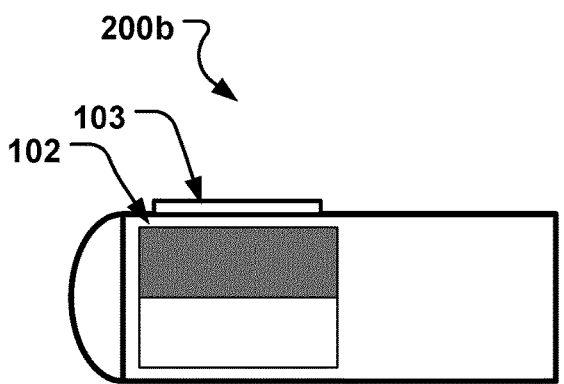
Fig. 2B
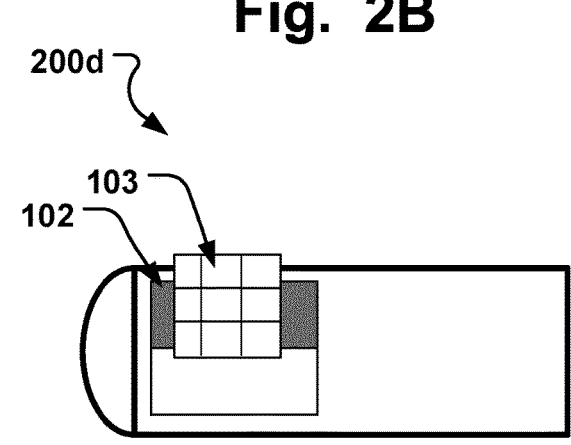
Fig. 2C
Fig. 2D
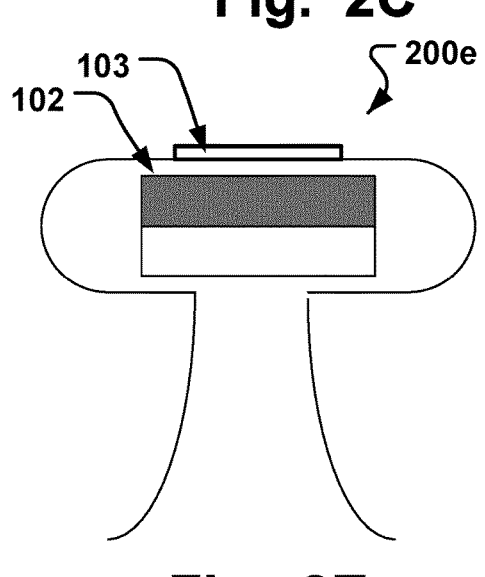
Fig. 2E
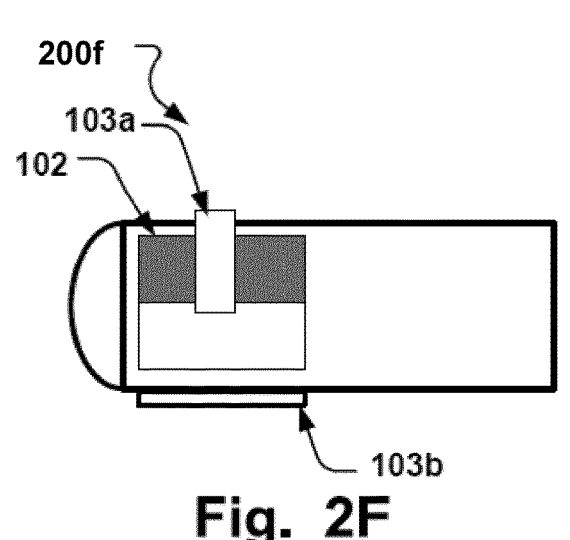
Fig. 2F

MAGNETOMOTIVE PROBE AND METHOD OF USE THEREOF

FIELD OF THE INVENTION

This invention pertains in general to the field of magnetomotive imaging. More particularly the invention relates to a magnetomotive imaging probe device. The magnetomotive imaging probe device is designed so that it could be to be arranged in a cavity of an animal or human, such as for transrectal or transvaginal use, but the device may also be designed or utilized for external use.

BACKGROUND OF THE INVENTION

Magnetomotive imaging is an imaging technique where superparamagnetic iron oxide nanoparticles can be used as ultrasound contrast agents. The main idea of this imaging technique is the application of a time-varying magnetic field (pulsed or sinusoidal) to the volume where the nanoparticles are deposited. The magnetic field induces movement of the particles and thereby the surrounding tissue, and the movement is detected with ultrasound. In early implementations, such as disclosed in Evertsson, M. et al, IEEE, Transactions on ultrasonic, ferroelectrics, and frequency control, vol. 60, no. 3, 1 Mar. 2013, pages 481-491, an electromagnet was employed to create the time-varying magnetic field, the electromagnet consisting of a coil around a cone-shaped iron-core, see FIG. 1. When a current is applied, a magnetic field is formed from the tip of the core. The force acting on the particles is dependent on the field strength, and on the field gradient.

Several problems exist with the electromagnet approach, in that the magnets tend to be heavy and demand high currents to produce a sufficient magnetic field, the later fact causing substantial heat. These facts make it difficult to produce magnetomotive systems that can be used clinically, especially in systems aimed for endoscopic applications. A magnetic field generator was proposed in EP 2801323, where a permanent magnet was used instead and that this magnet was rotated in such a way that north and south poles were alternately pointing towards the region where superparamagnetic nanoparticles had collected, and to that effect, exhibiting the particles to a varying magnetic force, attracting them alternately to the magnet.

The rotating permanent magnet solution was suggested as a magnetic field generator and separated from a standard ultrasound transducer connected to an ultrasound scanner. The device provided limited use due to its design and the limited range of the magnetic force.

Hence, a more user-friendly, compact and versatile magnetomotive imaging probe device, method and/or system which could be used at more locations on a human and/or animal would be an advantageous. Further improved sensitivity of detection of magnetic nanoparticles would also be an advantage together with improved patient safety, more cost-effective diagnosis.

SUMMARY OF THE INVENTION

Accordingly, examples of the present invention preferably seek to mitigate, alleviate or eliminate one or more deficiencies, disadvantages or issues in the art, such as the above-identified, singly or in any combination by providing a magnetomotive imaging probe assembly and a method for magnetomotive imaging with a probe assembly according to the appended patent claims.

According to a first aspect of the disclosure a magnetomotive imaging probe system is provided. The magnetomotive imaging probe device may comprise a housing having an outer surface and an inner cavity; a magnet; a sensing device configured to detect distance, movement, or magnetic material. The magnet may be arranged in the inner cavity of the housing and the sensing device may be arranged on the outer surface of the housing. The magnet may be arranged to generate a time-varying magnetic field at an imaging plane of the sensing device.

In some examples of the magnetomotive imaging probe, the sensing device may be an ultrasound transducer.

In some examples of the magnetomotive imaging probe, the magnet may be a cylindrically shaped permanent magnet and the time-varying magnetic field may be obtained by rotating the magnet.

In some examples of the magnetomotive imaging probe, the magnet may be a diametral magnet.

In some examples of the magnetomotive imaging probe, the ultrasound transducer may be arranged along a length of the magnet. Preferably, a length of the cylindrical magnet exceeds a width of the ultrasound traducer.

In some examples of the magnetomotive imaging probe, a distance between the magnet and the sensing device may be defined mainly by the thickness of the housing at the position of the sensing device and/or a distance between an inner surface of the housing and the magnet.

In some examples of the magnetomotive imaging probe, the magnet may be rotated using a motor.

In some examples of the magnetomotive imaging probe, the housing may have an elongated shape for positioning in a cavity of an animal, such as a human. The device may be configured for transrectal or transvaginal use.

In some examples of the magnetomotive imaging probe, the housing may be made of a non-electrically conductive material.

In some examples of the magnetomotive imaging probe, the ultrasound transducer may be an array, such as a linear array or a 2D array.

In some examples of the magnetomotive imaging probe, the array may be arranged concentrically with the magnet.

In some examples of the magnetomotive imaging probe, the housing may have a probe portion and a handle portion. The magnet and sensing device may be arranged at a distal portion of the probe portion and the motor may be arranged in the handle portion and may rotate the magnet via a shaft extending there between.

In some examples of the magnetomotive imaging probe, a sensor may be used for tracking the position of the magnet during the rotation. Other examples of sensors that may be used are sensors to detect probe position, temperature, acceleration or other physical parameters.

In some examples of the magnetomotive imaging probe, a disk may be arranged at each side of the magnet. Each disk may have a peg arranged in the center of each disk for holding the magnet. And one of the pegs may be configured for connecting to the motor or the shaft connected to the motor.

In some examples of the magnetomotive imaging probe, a packing, such as an O-ring, may be arranged at each side of the magnet for centering the magnet by use of the pegs.

According to another aspect of the disclosure, a method of magnetomotive imaging is described. The method may include introducing magnetic particles in tissue of a subject to be examined. The method may further include obtaining a time varying magnetic field using a magnet arranged in a cavity of a housing of a probe, the time varying magnetic field causing the magnetic particles to oscillate and/or move in an imaging plane of a sensing device arranged on an outer surface of the housing. The method may also include imaging the oscillation and/or movement of the particles using the sensing device. The method could also include e analyzing the oscillation and/or movement of the particles to determine a distribution of the magnetic particles.

In some examples of the method, using the determined distribution to provide aid in diagnosing the subject is described.

In some examples of the method, analyzing the distribution of the magnetic particles in lymph nodes for assessing if the lymph nodes are free from cancer is described.

In some examples of the method, rotating a permanent magnet to obtain the time varying magnetic field is described.

In some examples of the method, inserting the probe into an orifice of a subject to be diagnosed. Is described In some examples of the method, wherein the orifice is a rectum is described.

Some advantages with the described device are that the imaging and analysis of tissue of humans and large animals are made possible at more locations compared to the previous techniques. This without the most hampering drawback with the prior techniques which is that valuable magnetic field strength close to the ultrasound transducer is lost due to the separation of ultrasound transducer and magnet which improves the sensitivity of detection of magnetic nanoparticles.

Further embodiments of the invention are defined in the dependent claims, wherein features for the second and subsequent aspects of the invention are as for the first aspect mutatis mutandis.

It should be emphasized that the term "comprises/comprising" when used in this specification is taken to specify the presence of stated features, integers, steps or components but does not preclude the presence or addition of one or more other features, integers, steps, components or groups thereof.

BRIEF DESCRIPTION OF THE DRAWINGS

These and other aspects, features and advantages of which embodiments of the invention are capable of will be apparent and elucidated from the following description of embodiments of the present invention, reference being made to the accompanying drawings, in which

FIGS. 2A to 2F are schematic illustrations of different exemplary ultrasound transducer configurations at a distal portion of the probe;

DESCRIPTION OF EXAMPLES

Figures 1A, 1B, 1C:
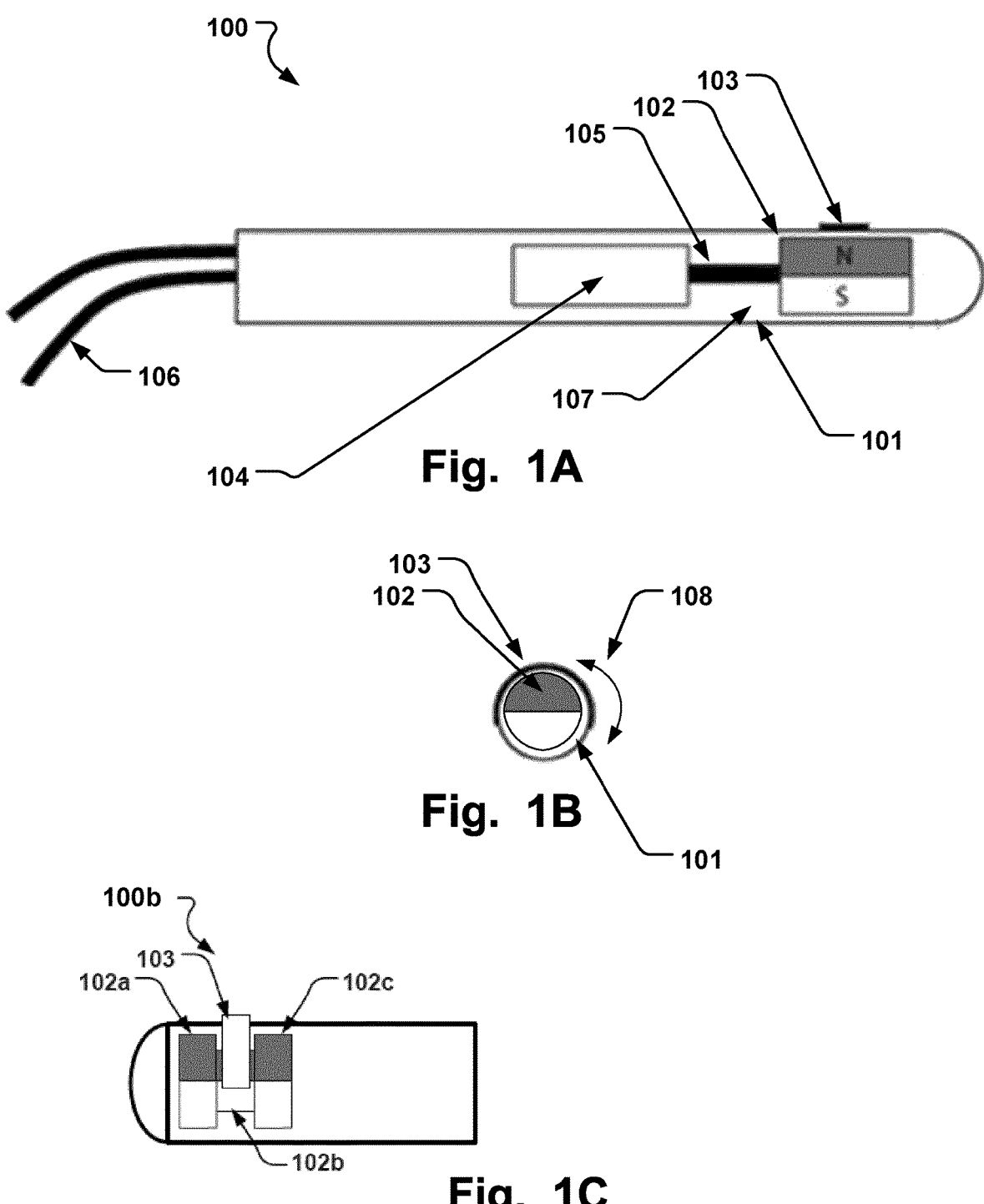
FIGS. 1A to 1C are illustrating a schematic magnetomotive imaging probe assembly according to an example of the present disclosure.

Specific examples of the disclosure will now be described with reference to the accompanying drawings. This disclosure may, however, be embodied in many different forms and should not be construed as limited to the examples set forth herein; rather, these examples are provided so that this disclosure will be thorough and complete, and will fully convey the scope of the disclosure to those skilled in the art. The terminology used in the detailed description of the examples illustrated in the accompanying drawings is not intended to be limiting of the disclosure. In the drawings, like numbers refer to like elements.

The following description focuses on an example of the present disclosure applicable to a probe assembly for magnetomotive imaging. However, it will be appreciated that the disclosure is not limited to this application but may be applied to many other fields and applications.

In magnetomotive imaging, a magnet is used to generate an inhomogeneous magnetic field. The inhomogeneous magnetic field may be a time-varying magnetic field at the same location as an imaging plane of an ultrasound transducer wherever the probe is positioned spatially relative the imaged subject. Magnetic nanoparticles, for example made from magnetite ($Fe_3O_4$), maghemite or zinc-doped magnetite, and usually with a size range of 10-100 nm (incl coating), are located at the target location within the imaging plane.

The time-varying magnetic field (T) is provided at a target location in the imaging plane of the ultrasonic transducer. Magnetic nanoparticles that are located at the target location in the imaging plane thus exhibit spatial fluctuations in the time-varying magnetic field (T) and are therefore forced to translate, displace, and/or rotate under the influence of the magnetic field (T). Because of the creation of the time-varying magnetic field component in the axial direction of the imaging plane, the displacement amplitude of the nanoparticles and their surrounding can be detected by the ultrasonic transducer. The time varying magnetic field may have a gradient which may cause the nanoparticles to translate, displace and/or rotate under the influence of the magnetic field (T). Therefore, the translatory or displacement motion of the particles may be oscillating due to the time variation of the magnetic field.

The shape of the particle may further enhance or suppress the action of translation, displacement, and/or rotation. For example, particles having an oval/elliptic shape may give rise to a rotational movement which together with a translational movement may be detectable with the ultrasound transducer and could be used to improve the detection. Spherical particles may also rotate due to the gradient of the time-varying magnetic field. Further, other shapes, such as rod shaped, octagonal or star shaped particles may also give rise to movements which may be used to improve the detection.

By observing the movement and displacement of the nanoparticles in the imaging plane an accurate representation of the concentration can be found which could be used to outline an object in the magnetomotive image or spots in a tissue with increased nanoparticle concentration.

The displacement of the nanoparticles may also be dependent on the distance between the magnet and where in the imaging plane the nanoparticles are positioned.

FIG. 1A is illustrating a schematic magnetomotive imaging probe device 100. The device includes a housing 101 having an outer surface and an inner cavity 107. The device may further include a magnet 102 arranged in the inner cavity 107 of the housing 101. The magnet 102 is configured for generating a time-varying magnetic field. The magnet 102 may be a cylindrically shaped permanent magnet, preferably a diametrically magnetized magnet. Such a diametral magnet is a cylindrically shaped magnet, having a rotational axis extending in a lateral direction. This type of magnet provides a magnetic field orthogonally to the axis. In some example may the shape of the magnet be a rectangular cuboid, such as a cube, rotating around an axis and provides a magnetic field orthogonally to the axis, similar as for a diametral magnet. The magnet has opposite magnetic poles (N, S) separated along a diameter of the magnet in the radial direction (r), whereby rotation of the magnet, create a time-varying magnetic field (T), at a target location. It is conceivable that other shapes of the magnet 102, may provide the same effect.

The time-varying magnetic field may be obtained by rotating the magnet 102 using a motor 104. The magnet 102 may be rotated by the motor 104 via a shaft 105. Alternatively, in some examples may an electric magnet be used, and the time-varying magnetic field may be obtained by switching the poles, driving a sinusoidal current, or any time-varying current that results in the desired magnetic field.

For detecting the translation displacement and/or rotation of the particles, a distance, movement, or magnetic material sensing device 103, for example an ultrasound transducer, such as an ultrasound array, an optical sensor (for example laser Doppler), a susceptometer, or other means for detecting distance, movement, or magnetic material known to the person skilled in the art, may be used. For the rest of this application, an ultrasound transducer will be used as an example of a sensing device, but as described other types of sensing devices could be used instead.

The ultrasound transduced may be arranged on the outer surface of the housing 101 so that an imaging plane of the ultrasound transducer 103 is within the time-varying magnetic field. In particular, this may be achieved by arranging an ultrasound transducer 103 on an outer surface of the housing 101 so that the ultrasound transducer 103 is positioned along a length of the magnet 102. Preferably a length of the cylindrical magnet 102 exceeds a width of the ultrasound transducer 103. The ultrasound transducer 103 will then be positioned within the time varying magnetic field together with the imaging plane of the ultrasound transducer 103. This arrangement may increase the sensitivity of detection of magnetic nanoparticles inside the volume of the magnetic field moving due to the variation of the magnetic field.

Typically, ultrasound pulses in the geometric shape of a beam, are fired using a number of the elements in the array, whereby a focused beam may be achieved by delaying the transmission of certain elements such that the sound interferes constructively at the focus. Likewise, the returning echoes may be detected on a number of elements, and a reconstructed signal may be achieved such that echoes along the transmit beam are amplified, by the same delays as in the transmit case. Typically, the magnetic particles are much smaller than the resolution cell of the ultrasound, but their displacement upon the action of the magnetic field, may create a detectable motion in their immediate surrounding, such that the motion can be detected by ultrasound. This can be done by covering the imaging plane by imaging beams at a rate exceeding that of the magnetic field frequency. Theoretically the rate of imaging (probing) at one location must be at least twice that of the induced motion of the nanoparticles, but practically even higher, 4-10 times for instance. Other imaging schemes are possible, such as creating a plane wave insonifying a large portion of the region to be imaged.

The sensitivity may be further enhanced by arranging the magnet 102 and the ultrasound transducer 103, in such a way that the active ultrasound elements are situated as close as practically possible to the magnet 102. When the ultrasound transducer is arranged on the housing, as illustrated in FIGS. 1A to 10, a distance between the magnet 102 and the ultrasound transducer 103 may be defined mainly by the thickness of the material of housing 101 at the position of the ultrasound transducer and/or a distance between an inner surface of the housing and the magnet 102.

FIG. 1A shows the case for a rotating permanent magnet 102, magnetized diametrically, whereby a multitude of ultrasound elements are arranged in an arc that is concentric with the rotation axis of the magnet 102. This concentric arrangement is also illustrated in FIG. 1B. Upon rotation of the magnet 102, the magnetic field at a point some distance from the probe 100, may also rotate and induce a rotating motion to magnetic particles located at that point. In FIGS. 1A and 1B, the imaging plane is orthogonal to the rotation axis 108 of the magnet 102.

The probe 100 may further include connectors 106, such as cables, for controlling the probe and for transferring recorded data, such as imaging data from the ultrasound transducer 103 to a computer or a control unit which includes a processor. Additionally, and/or alternatively, the probe may be controlled, and the data may be transferred wirelessly, such as over Wi-Fi or other types of wireless protocols, such as Bluetooth.

Additionally, and/or alternatively, the cables 106 may be used for providing power to the probe. Alternatively, the power to the probe may be provided using batteries arranged in the probe.

The motor 104 of the magnetomotive imaging probe device 100 may be controlled by a control unit (not shown). As described above, the motor 104 may be coupled to the control unit via the connectors 106 or through a wireless protocol. The power of the motion of the magnet 102 may then be controlled. The control unit may be adapted to vary the speed of motion (w) of the magnet 102, according to a predetermined pattern to thereby vary the frequency of the time-varying magnetic field (T) as a predetermined impulse to generate an impulse response of magnetic nanoparticles at the target location. This provides for determining an impulse response from the nanoparticles that may be indicative of the material properties, such as viscosity and density. Hence the nanoparticles may be displaced by the magnetic impulse and the material properties will affect how the displacement varies over time, such as the dominant frequency, maximum amplitude, and speed of damping may be indicative of material density, the elasticity and viscosity.

The control unit may be adapted to vary the speed of motion (w) of the magnet 102, such as by increasing the speed linearly up to a certain maximum speed, and thereafter decrease the speed, to provide a sweep throughout frequencies (chirp) and detect the resulting displacement amplitude of the nanoparticles. The control unit may thus be adapted to vary the speed of motion (w) of the magnet 102, according to such predetermined pattern to provide for detection of a frequency impulse response. The control unit may be adapted to set a constant speed of motion (w) of the magnet 102. Depending on the position of the S-pole relative the N-pole during rotation of the magnet the rotational force may vary, for instance due to influence of the earth magnetic field or iron structures in the proximity, which thus may be compensated by the control unit.

The control unit may be further adapted to synchronize the frequency or speed of motion (w) of the magnet 102, to the ultrasound imaging in order to provide for ultrasound detection at the magnetic field frequency (that of the magnetic field time-variation), and further to allow for detection at the phase of the magnetic field relative the ultrasound imaging.

The ultrasound transducer 103 may also have an ultrasound control unit (not shown) that provides for the necessary control and analysis related to the ultrasound equipment.

The device may include different sensors, for example a sensor for tracking the position of the magnet during the rotation. This could be an encoder for detecting a pulse on each rotation. This may be useful for synchronize the frequency or speed of motion (w) of the magnet 102, to the ultrasound imaging or when having a gearbox, such as reduction gear.

Other sensors that could be used are, an accelerometer to detect if the device is held steady or is moving, a gyroscope, thermometer, a pH sensor, a sensor for detecting interfering magnet fields.

The housing should be made of a non-electrically conductive material to avoid eddy currents which may reduce the delivered magnetic field. One such material is Polyether ether ketone (PEEK). Other materials could be Polyphenylene sulfide (PPS), or polysulfone.

FIG. 10 is illustrating an alternative design 100b of a magnet compared to the design illustrated in FIGS. 1A and 1B. Instead of a magnet having a cylindrical shape with a constant diameter along the length of the magnet, the magnet may have a cylindrical shape with at least two different diameters. For example, a magnet may consist of two portions, such as a first portion 102b arranged as illustrated in FIGS. 1A to 1B and a second portion 102a,102c arranged at a side of the first portion 102b. The second portion 102a, 102c may thereby be arranged adjacent to, but at a side of, the array 103. The second portion 102a, 102c may have a diameter different from the first portion 102b, such as the diameter of the second portion 102a, 102c being larger than the diameter of the first portion 102b.

In some examples, the magnet may exist of three portions 102a, 102b, 102c as illustrated in FIG. 10. The second portion 102a and the third portion 102c may have a diameter which differ from the first portion 102b, for example, the diameters of the second portion 102a and the third portion 102c may be larger than the diameter of the first portion 102b. In some examples the magnet may have the second and third portion 102a, 102c equally sized diameters.

Additionally, and/or alternatively, in some examples of the magnet design, the magnet may only comprise of one or two of the side portions 102a, 102c arranged adjacent to, but at a side of, the array 103.

By adding cylindrical portions 102a, 102c with a larger diameter to the magnet, and wherein the cylindrical portions 102a, 102c are arranged on the sides of the array 103, the range of the magnetic force may be extended. The larger magnetic volume of the magnets 102a and 102c, gives a larger force at a given distance, compared to a single magnet with the diameter of 102b.

The effect of the magnetic field on a particle depends on the angle and the distance, therefore in examples where a magnet is only arranged on the side of the array 103, such as a magnet only comprising at least of the elements 102a, 102c, the magnetic field may, when compared to a magnet arranged beneath or over the array 103, affect a particle with a less degree closer to the array 103 but at a distance of a few cm away from the array 103 the relative difference may decrease.

The void in the probe body which may be provided between the smaller diameter magnet 102b and the housing, may be used for interface electronics or acoustic backing materials. The magnet 102 may be manufactures as a single solid structure; or be manufactured by arranging separate portions of the magnet side by side. When making the magnet from separate portions, an adhesive may be used to fasten the portions to each other. Alternatively, the magnetic force may be strong enough to hold the portions together.

The diameters may vary as well as the number of cylindrical elements, as well as their polarity.

FIGS. 2A to 2F are schematic illustrations of different exemplary ultrasound transducer configurations in relation to the magnet at a distal portion of the probe device. The transducer is in these examples different types of arrays. An array could be a single array, such as a single linear array, with a number of ultrasound elements located along a line. The number of elements could be, as an example, between 128 to 256 depending on the size of the elements and the length of the array. A lower or higher number of elements may be used.

FIG. 2A is illustrating schematically an ultrasound array 103 arranged similar as in FIGS. 1A to 1C wherein the ultrasound array 103 is concentrically arranged with an axis of the magnet 102. As an example, for an array 103 that has between 128 and 256 elements and a central frequency, for instance in the range of, 5 to 25 MHz, such as 5 to 20 MHz, such as 7 to 15 MHz, such a 10 MHz, this arrangement may cover approximately 160-230 degrees field of view. As a further example, if the array 103 has 192 elements, this arrangement may cover approximately 180 degrees field of view, given an ultrasound center frequency of, for instance in the range of, 5 to 25 MHz, such as 5 to 20 MHz, 7 to 15 MHz, such as 7 to 8 MHz. The field of view may depend on the dimensions of the probe and the estimates given are for a probe to be used for transrectal or transvaginal applications.

FIG. 2B is illustrating schematically an ultrasound array 103 arranged orthogonally compared to the configuration illustrated in FIG. 2A. This means that the length of the array 103 is arranged along the length of the magnet 102.

FIG. 2C is illustrating schematically a combination of at least two arrays wherein a first ultrasound array 103a is arranged as in FIG. 2A and a second ultrasound array 103b is arranged as in FIG. 2B.

FIG. 2D is illustrating schematically a 2D array. The 2D array 103 is arranged concentrically with an axis of the magnet 102 but will record an image in two dimensions similar as the use of two arrays 103a, 103b illustrated in FIG. 2C. Alternatively of a single 2D array 103, the array 103 may comprise a plurality of single arrays, such as single linear arrays. Such an arrangement is sometimes called a 1.5D array. 1.5D arrays are used to provide improved focusing in the elevation direction of the imaging plane (the plane thickness in other words). The improved focus may be obtained by a number of array rows (for example 3-7) adjacent to the center array, for example by progressively increasing the difference in transmit (or receive) delays between different rows in the array, along the 0.5-direction, the beams may be focused in the elevation direction. By varying the delays, the focus may be placed at different depths along the beam axis, and multiple transmits will achieve a total thinner imaging plane by using only the data from the focused parts of the beams. The same delays may be applied on receive to achieve improved elevational focusing also on receive.

FIG. 2F is illustrating schematically a combination of at least two arrays 103a, 103b wherein a first array 103a is arranged on one side of the probe housing and a second array 103b is arranged at an opposite side of the probe housing. Each of the at least two arrays 103a, 103b may provide an imaging plane extending from the respective array. The arrays 103a, 103b may be oriented orthogonally on the probe support, as in FIG. 2F, to provide one plane including the rotational axis of the magnet, or any parallel line, and another plane, orthogonal or angled to said axis. Thus, orthogonal planes of the same target may be examined, simply by rotating the probe, providing a fuller understanding of tissue morphology.

FIG. 2E is illustrating a different type of distal end of the probe. While FIG. 1A to 10 as well as FIGS. 2A to 2D and 2F are illustrating elongated devices which may be used, mainly, in a cavity of an animal or a human, such as for transrectal or transvaginal use. The illustrated device may improve external usage, such as on skin examination, that is for a transcutaneous ultrasound examination. The ultrasound array 103 could be arranged as illustrated in any of FIGS. 2A to 2D and 2F in relation to the magnet 102.

Figures 3, 4:
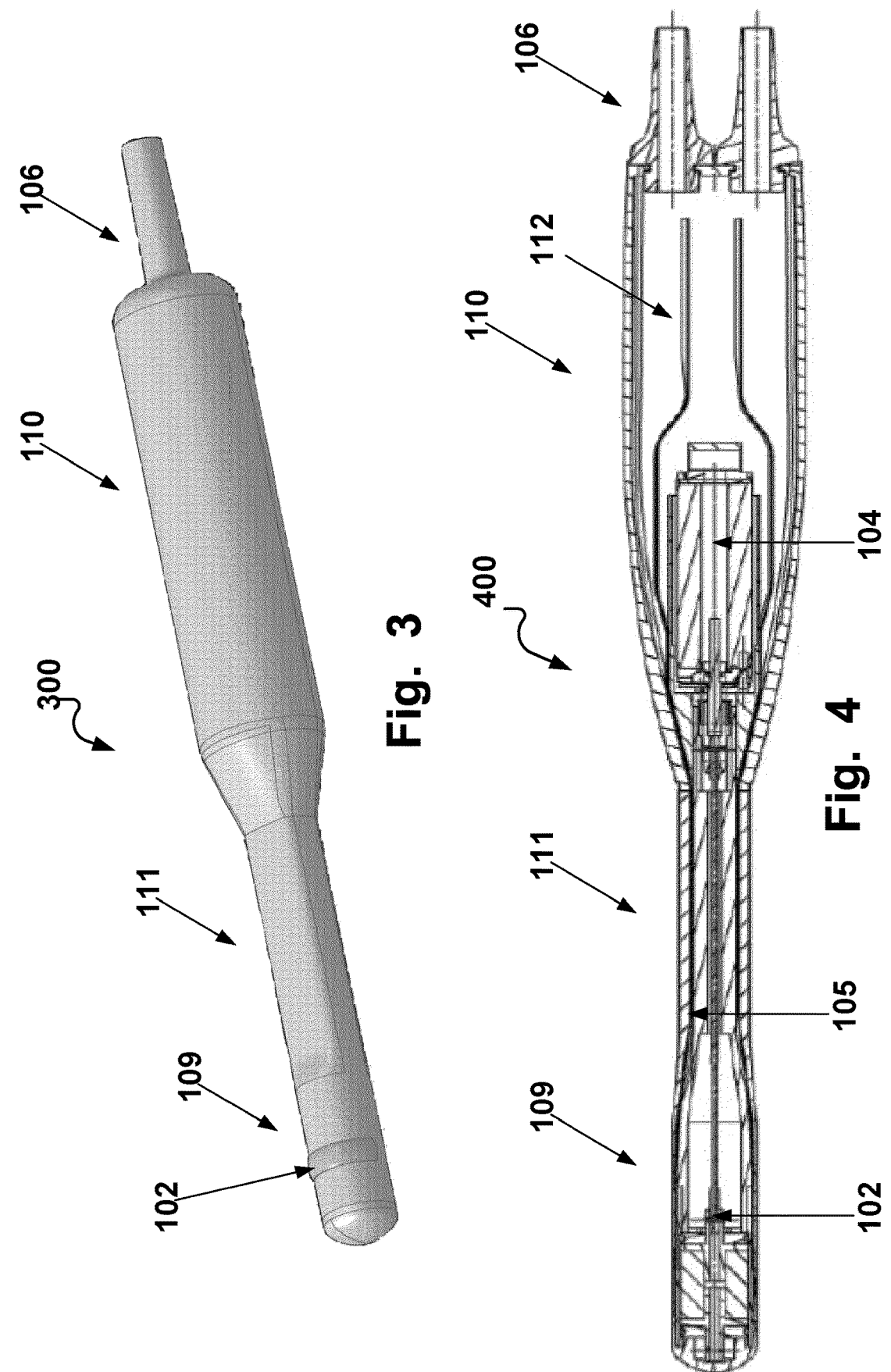
FIG. 3 is illustrating a schematic example of an outer housing of the probe according to the disclosure.
FIG. 4 is illustrating a schematic example of cross-section of the probe illustrated in FIG. 3.

FIG. 3 is illustrating a schematic example of an outer housing 300 of the probe according to an example of the disclosure. The probe includes a distal portion 109 and a handle portion 110. At the distal portion 109, the ultrasound transducer 102 is arranged. The probe 300 may further include at least one connector 106 and/or a power cord. The distal portion 109 and the handle portion 110 may be connected via a neck portion 111. The neck portion 111 may have a smaller diameter compared to the distal portion 109. The probe 300 illustrated in FIG. 3 is made elongated and as smooth as possible as well as being dimensioned to be inserted into a cavity of a human or animal, such as transrectal or transvaginal. The device is not limited to be used in a cavity but could also be used externally.

To make the device comfortable, the distal portion 109 and the neck portion 111 have to be made "slim". Slim depends on the cavity but or transrectal use and for transvaginal use, the diameter should preferably be less than 30 mm, such as 25 mm, such as less than 20 mm, such as about 15 mm.

To further improve the positioning of the device in a cavity, a disposable sleeve may be arranged over the distal portion 109 and the neck portion 111 before being inserted into the cavity.

Alternatively, the distal portion may have a different shape for external use, such as having a broader tip to improve handling of the device, see for example FIG. 2E.

FIG. 4 is illustrating a schematic example of cross-section 400 of the probe illustrated in FIG. 3. As illustrated, the magnet 102 and the also the ultrasound transducer 109 is positioned as close as possible to the distal end of the distal portion 109. The motor 104 is positioned in the handle portion 110 and the shaft 105 connecting the magnet 102 and the motor 104 is arranged through the neck portion 111. For connecting and controlling the ultrasound transducer 102, a printed circuit board 112 is running through the device.

Figure 5A:
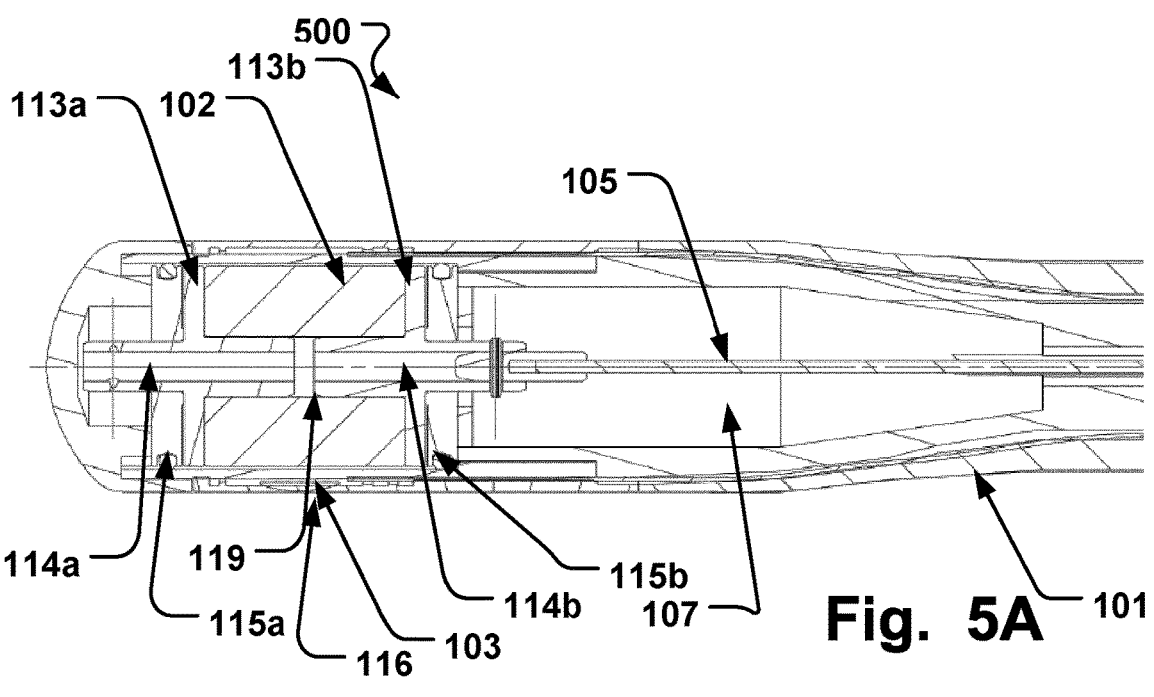
FIG. 5A to 5C are illustrating a schematic example of the magnet and ultrasound arrangement according to the disclosure.
Figure 5B:
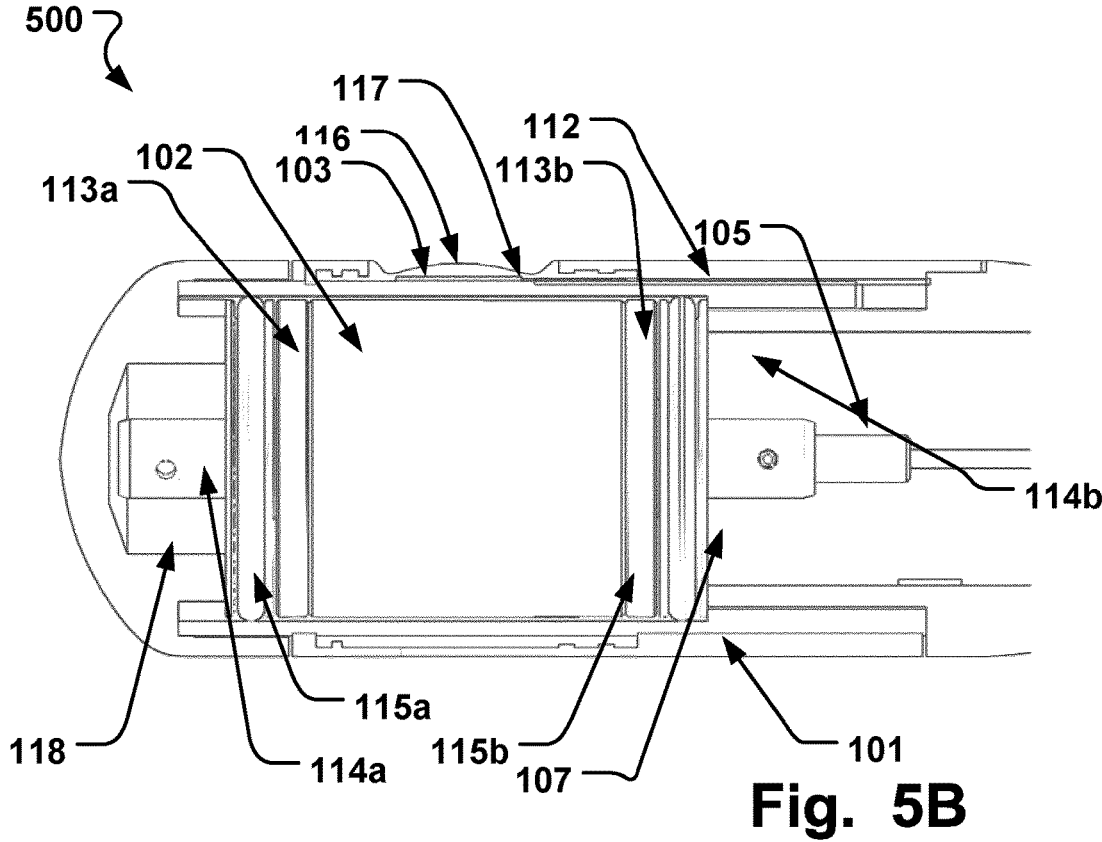
Figure 5C:
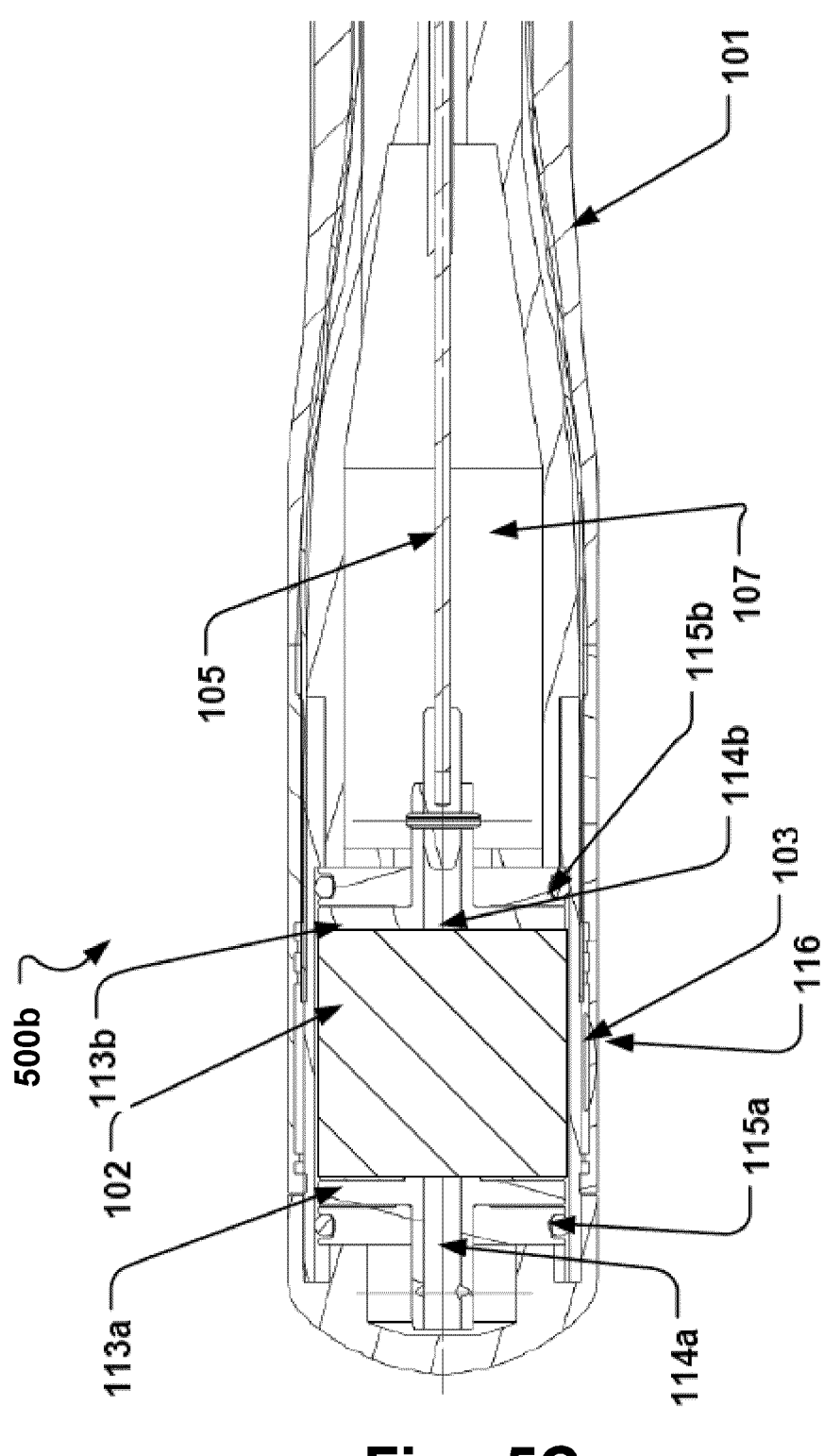

FIGS. 5A to 5C are illustrating a schematic example 500, 500b of the magnet and ultrasound arrangement according to the disclosure. FIGS. 5A and 5B are illustrating cross-sectional views of an example of the ultrasound and magnet configuration.

The magnet 102 is arranged in the cavity 107 of the distal portion of the probe device. The cavity 107 is in the illustrated example a lumen which runs through the housing 101. On each side of the magnet 102 a disk 113a, 113b is arranged. The disk is preferably permeable to the magnetic field. Each disk 113a, 113b has a peg 114a, 114b. The disks 113a, 113b and the pegs 114a, 114b are used to hold the device. the pegs 114a, 114b runs through a central lumen 119 of the magnet 102. To minimize the vibrations, the lumen 119 should run straight through the very center of the magnet 102. One way of achieving this with a low tolerance may be to arrange the disks 113a, 113b, with the pegs 114a, 114b, on the magnet 102 before the magnet is lathed into its shape. By holding the magnet by the disks 113a, 113b and the pages 114a, 114b during the lathing, a high accuracy can be obtained.

To further minimize any vibrations when rotating the magnet 102, a packing 115a, 115b, such as an O-ring, may be arranged at each side of the magnet 102 for centralizing the magnet 102 in the lumen 107 using the pegs 114a, 114b. the most distal peg 114a may be arranged in a holder 118 while the proximal peg 114b may be connected to the motor via shaft 105.

The ultrasound transducer 103 is arranged on an outer surface of the housing 101. In this way, the distance between the ultrasound transducer 102 and the magnet 102 may be minimized and is mainly composed of the thickness of the housing wall at the position between the magnet 102 and the ultrasound transducer 103. The distance may also be determined by a space between the magnet 102 and an inner surface of the housing 101. This distance may be determined by the tolerance required for rotating the magnet 102.

Since the ultrasound transducer 103 needs to be controlled, such as synchronization with the magnet, and transferring data to a control unit, such as a computer, etc. a printed circuit board, PCB, 112 may need to be connected to the ultrasound transducer 103. The ultrasound transducer is also arranged on a plate used for retaining the transducer to the housing. A notch 117 may therefore be made outer surface of housing 101 surrounding magnet 102. In the notch 117, the components used for retaining the ultrasound transducer 103 as well as the connection to the PCB may be arranged, thus the part of these components which are arranged underneath the transducer, such as between the ultrasound transducer 103 and the magnet 102, may compose part of the thickness of the housing 101 at the location of the ultra sound transducer. The notch may therefore assist in minimizing the distance between the ultrasound transducer 103 and the magnet 102.

In total, the distance between the ultrasound transducer 103 and the magnet 102 may be less than 2 mm, such as less than 1.5 mm such as 1 mm.

Additionally, the ultrasound transducer 116 may have a lens arranged on top for focusing the waves.

FIG. 5C is illustrating a schematic example 500b of the magnet and ultrasound arrangement which is similar to the arrangement in FIGS. 5A and 5B. The difference is that the magnet 102 is solid in FIG. 5C and does not include the lumen running straight through the very center of the magnet 102, as illustrated in FIG. 5A. Instead for the disks 113a, 113b, arranged on each side of the magnet, having two pegs, one protruding into the lumen to connect the disks 113a, 113b to the magnet 102 and one protruding outwards to connect the magnet to the shaft 105 and to the holder 118, as in FIG. 5A, the disk 113a, 113b may be connected to the magnet 102 through other means. For example, the disks 113a, 113b may be adhered to the magnet using an adhesive, such as a glue. Alternatively, and/or additionally, in some examples, the disks 113a, 113b may be fastened to the magnet using bolts or screws. Other examples may be to connect the disks 113a, 113b to the magnet 102 by friction obtained through pressure applied by the shaft. Depending on the materials of the disks 113*a*, 113*b*, the disks 113*a*, 113*b* may be connected by adhesive forces, such as molecular forces.

The advantage of using a solid magnet is that the magnetic force may be stronger compared to a similar sized magnet having a lumen through the center. This may be due to the increased volume of material.

The magnetic force is also dependent on the material properties and some materials provide a stronger magnetic force than other materials. Examples of materials are NdFeB (Neodymium Iron Boron) either sintered or bonded having a standard value of N42 or higher, such as N45, N48, N50 or N52. Other materials with strong magnetic force may be Iron-nitride (FeN).

Additionally, to have only a magnetic field varied with the time, a static magnetic field may also be applied simultaneously. Since the magnetic force acting on particles is proportional to both the field strength and the field gradient, a second magnetic field being stationary may increase the magnetic force. The field strength of the second magnetic field may be below magnetic saturation of the particles. The second magnetic field may be applied using an electromagnet. The electromagnet may be stationary coils, which after applying a DC-current through them, will produce a field that can pre-magnetize the particles to increase the oscillating force.

Alternatively, instead of a static second magnetic field, the field may be time varied in relation to the time varied field provided by the magnet on the probe. For example, the variation of the second magnetic field, provided by the additional magnet, may be related to a rotation of the magnet inside the probe. For example, the variation of the second magnetic field, provided by the additional magnet, may be synchronized with the time variation of the magnet inside the probe, such as synchronized with the rotation of the magnet inside the probe. Synchronized may involve a difference in phase and/or amplitude between the two time varying field. When the magnet inside the probe is a rotating permanent magnet, a sensor for tracking the position of the magnet may be used for controlling the time variation of the second magnetic field. The time variation of the second magnetic field may be obtained by having a stationary coil and varying a DC current or applying an AC-current.

In some examples, the second magnet may be used to obtain a counteracting force to the earth magnetic field. This may be done by a static magnetic field. In the examples where a varied current is applied to the second magnet a static component can be applied simultaneously.

The additional magnet may be part of the probe or as part of a system where the additional second magnet may be arranged as a separate unit, such as arranged in the examination room, in an examination table.

Figure 6:
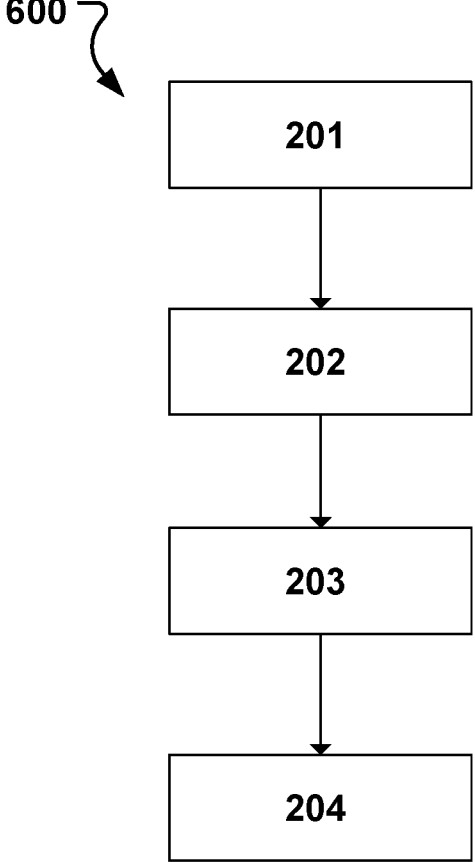
FIG. 6 is illustrating a flowchart of an exemplary method according to the disclosure.

FIG. 6 is illustrating a flowchart of an exemplary method 200. The method may be used to examine or diagnose a subject. The method 200 may include introducing 201 the magnetic nanoparticles in tissue of the subject. The particles may be introduced intravenously or subcutaneously.

The method 200 may also include generating 202 a time-varying magnetic field (T) at an imaging plane of the sensing device 103, such as an ultrasound transducer.

The method 200 may further comprises detecting or imaging 203 motion of magnetic nanoparticles in response to the time-varying magnetic field with the sensing device 103 in the imaging plane. This may include detecting or imaging the oscillation and/or movement of the particles using the sensing device.

As mentioned above, analyzing 204 the oscillation and/or movement of the particles to determine a distribution and/or concentration of the magnetic particles may provide for an accurate determination of nanoparticle concentration and/or distribution, and further improved analysis of the examined material.

Determining the concentration and/or distribution of the particles may provide aid for a practitioner to assess the status of tissue, such as when assessing if the tissue is free from tumors, cancer and/or metastasis. One such area is to determine if lymph nodes are free from cancer.

The method 200 may further include rotating the cylindrical permanent magnet 102 according to a predetermined pattern to thereby vary the frequency of said time-varying magnetic field (T) as a predetermined frequency impulse to generate a frequency impulse response of the magnetic nanoparticles. The properties of the material of the analyzed object may thus me determined. The predetermined pattern may for example include rotating the magnet with a certain number of turns, or fractions of turns, such as half a turn, during a period of time such as a certain number, or fractions of seconds or minutes, to subsequently detect the response from the nanoparticles.

The method 200 may alternatively, and/or in addition comprise rotating the cylindrical permanent magnet 102 with a constant rotational speed.

The method 200 may alternatively, and/or in addition comprise rotating the cylindrical permanent magnet 102 with a varied rotational speed.

As will be appreciated by one of skill in the art, the present invention may be embodied as device, system, or method.

The present disclosure has been described above with reference to specific embodiments. However, other examples than the above described are equally possible within the scope of the invention. Different method steps than those described above, may be provided within the scope of the invention. The different features and steps of the invention may be combined in other combinations than those described. The scope of the disclosure is only limited by the appended patent claims.

More generally, those skilled in the art will readily appreciate that all parameters, dimensions, materials, and configurations described herein are meant to be exemplary and that the actual parameters, dimensions, materials, and/or configurations will depend upon the specific application or applications for which the teachings of the present invention is/are used.

The invention claimed is:

1. A magnetomotive imaging probe device, comprising:
a housing having an outer surface and an inner cavity;
a magnet; and
a sensing device configured to detect distance, movement, or magnetic material;
wherein the magnet is arranged in the inner cavity of the housing and the sensing device is arranged on the outer surface of the housing, wherein a distance between the magnet and the sensing device is defined mainly by the thickness of the housing at the position of the sensing device and/or a distance between an inner surface of the housing and the magnet, wherein the magnet is arranged to generate a time-varying magnetic field at an imaging plane of the sensing device, and wherein the imaging plane extends outside of the housing.

2. The magnetomotive imaging probe of claim 1, wherein the sensing device is an ultrasound transducer.

3. The magnetomotive imaging probe of claim 1, wherein the magnet is a cylindrically shaped permanent magnet having at least one diameter, and wherein the time-varying magnetic field is obtained by rotating the magnet.

4. The magnetomotive imaging probe of claim 3, wherein the magnet has at least two portions with different diameters.

5. The magnetomotive imaging probe of claim 3, wherein the magnet is a diametral magnet.

6. The magnetomotive imaging probe of claim 2, wherein the ultrasound transducer is arranged along a length of the magnet.

7. The magnetomotive imaging probe of claim 3, wherein the magnet is rotated using a motor.

8. The magnetomotive imaging probe of claim 1, wherein the housing has an elongated shape for positioning in a cavity of an animal.

9. The magnetomotive imaging probe of claim 2, wherein the ultrasound transducer is an array, such as a linear array, at least two linear arrays, a 1.5D array or a 2D array, wherein the array is arranged concentrically with the magnet.

10. The magnetomotive imaging probe of claim 7, wherein the housing has a probe portion and a handle portion, wherein the magnet and sensing device is arranged at a distal portion of the probe portion and the motor is arranged in the handle portion and rotates the magnet via a shaft.

11. The magnetomotive imaging probe of claim 2, wherein a sensor is used for tracking the position of the magnet during the rotation.

12. The magnetomotive imaging probe of claim 2, wherein at least one disk is arranged at at least one side of the magnet, wherein the at least one disk has a peg arranged in the center of the at least one disk for holding the magnet.

13. The magnetomotive imaging probe of claim 2, wherein a disk is arranged at each side of the magnet being fastened or adhered to the magnet, wherein the magnet is solid.

14. A system comprising a magnetomotive imaging probe of claim 1, and a second magnet, wherein the second magnet is an electromagnet providing either a static magnetic field or a time varying magnetic field in relation to a rotation of a first permanent magnet arranged in a housing of the magnetomotive imaging probe.

15. A method of magnetomotive imaging, comprising:
introducing magnetic particles in tissue of a subject to be examined;
obtaining a time varying magnetic field using a magnet arranged in a cavity of a housing of a probe, the time varying magnetic field causing the magnetic particles to oscillate and/or move in an imaging plane of a sensing device arranged on an outer surface of the housing, wherein a distance between the magnet and the sensing device is defined mainly by the thickness of the housing at the position of the sensing device and/or a distance between an inner surface of the housing and the magnet, and wherein the imaging plane is outside of the housing;
imaging the oscillation and/or movement of the particles using the sensing device; and
analyzing the oscillation and/or movement of the particles to determine a distribution of the magnetic particles.

16. The method of claim 15, analyzing the distribution of the magnetic particles in lymph nodes for assessing if the lymph nodes are free from cancer.

17. The method of claim 15, comprising rotating a permanent magnet to obtain the time varying magnetic field.

18. The method of claim 15, inserting the probe into an orifice of a subject to be diagnosed.

19. The method of claim 15, obtaining a second magnetic field using an external magnet, wherein the magnetic field of the second magnet is static and/or time varying.

20. A magnetomotive imaging probe device comprising:
a housing having an outer surface and an inner cavity;
a magnet; and
a sensing device configured to detect distance, movement, or magnetic material;
wherein the magnet is arranged in the inner cavity of the housing and the sensing device is arranged on the outer surface of the housing, wherein the magnet is arranged to generate a time-varying magnetic field at an imaging plane of the sensing device, and wherein the housing has an elongated shape that is configured for transrectal or transvaginal use.

* * * * *